(12) United States Patent
Seifert

(10) Patent No.: US 6,344,323 B1
(45) Date of Patent: Feb. 5, 2002

(54) COMPOSITIONS AND METHODS FOR INHIBITING COX-2 EXPRESSION AND TREATING COX-2 ASSOCIATED DISORDERS BY USING COX-2 ANTISENSE OLIGONUCLEOTIDES

(75) Inventor: Wilfried Seifert, La Jolla, CA (US)

(73) Assignee: Vitagenix, Inc., LaJolla, CA (US)

( * ) Notice: Subject to any disclaimer, the term of this patent is extended or adjusted under 35 U.S.C. 154(b) by 0 days.

(21) Appl. No.: 09/397,168

(22) Filed: Sep. 16, 1999

Related U.S. Application Data

(60) Provisional application No. 60/100,590, filed on Sep. 16, 1998.

(51) Int. Cl.[7] .......................... C12N 15/00; C12Q 1/68; A61K 48/00
(52) U.S. Cl. .......................... 435/6; 435/325; 435/366; 435/375; 536/23.1; 536/24.5; 536/25.3; 514/44
(58) Field of Search .......................... 435/6, 7.21, 91.1, 435/91.31, 325, 366, 375, 320.1; 536/23.1, 24.1, 24.3, 24.5; 514/44

(56) References Cited

U.S. PATENT DOCUMENTS

| | | | |
|---|---|---|---|
| 5,814,500 A | * | 9/1998 | Dietz ...................... 435/172.3 |
| 5,859,229 A | | 1/1999 | Kniss ........................ 536/24.5 |
| 6,048,850 A | | 4/2000 | Young et al. ............... 514/183 |

FOREIGN PATENT DOCUMENTS

| WO | WO 95/16466 | * | 6/1995 |
|---|---|---|---|

OTHER PUBLICATIONS

Stein, Nature Biotech. 17: 209, Mar. 1999.*
Branch, TIBS 23:45–50, Feb. 1998.*
Flanagan et al., Nature Biotech 17:48–52, Jan. 1999.*
Crooke, *Antisense Research and Application*, pp. 1–50, 1998.*
Uhlmann et al, Chem Rev 90 (4): 543–584, Jun. 1990.*

\* cited by examiner

*Primary Examiner*—Andrew Wang
*Assistant Examiner*—Mary Schmidt
(74) *Attorney, Agent, or Firm*—Fish & Richardson P.C.

(57) ABSTRACT

The invention features antisense oligonucleotide molecules that specifically bind polynucleotides encoding COX-2. The present invention provides antisense oligonucleotides capable of inhibiting COX-2 expression, and methods of use thereof to reduce activity of COX-2 in tissues in order to treat diseases such as, for example, rheumatoid arthritis, inflammatory bowel disease, multiple sclerosis, chronic liver disease, ulcerative colitis, cell proliferative disorders, and inflammation associated with Alzheimer's Disease and stroke.

35 Claims, No Drawings

COMPOSITIONS AND METHODS FOR INHIBITING COX-2 EXPRESSION AND TREATING COX-2 ASSOCIATED DISORDERS BY USING COX-2 ANTISENSE OLIGONUCLEOTIDES

CROSS REFERENCE TO RELATED APPLICATIONS

This application claims priority from U.S. Provisional Application Serial No. 60/100,590 filed Sep. 16, 1998, the disclosure of which is incorporated herein by reference.

FIELD OF THE INVENTION

This invention relates generally to the field of therapeutic compositions and more specifically to antisense oligonucleotides that bind to Cyclooxygenase-2 (COX-2) polynucleotides and methods of treatment for diseases associated with COX-2.

BACKGROUND OF THE INVENTION

Eicosanoids are described as paracrine hormones derived from C20 fatty acids and released from membrane lipids in response to cellular signals. Those compounds are divided into two groups: leukotrienes and prostanoids, both formed from arachidonic acid (AA) by two distinct enzymatic pathways. Prostaglandin synthase (cyclooxygenase, cox) is the main enzyme that catalyzes the first biosynthetic steps of prostanoids conversion from AA. First, the oxidation of AA to prostaglandin G2 and second, the reduction to prostaglandin H2, which is a common precursor for all prostaglandins (PGs), thromboxanes (TBs) and prostacyclines (PIs). The purification of prostaglandin synthase and characterization of its biological activity was first reported in the 1970's (1), however the first ovine cDNA sequence was cloned a decade later (2). This information was used to clone the human gene (3), which is 25 kilobases (kb) long and contains eleven exons separated by ten introns and produces 2.8 kb long mRNA (4). Until the beginning of this decade it was believed that only one cox gene existed. For many years it was assumed that prostaglandin generation in response to cellular stimulation was limited by AA availability or due to the constitutively expressed enzyme (cox-1) (5). However, the studies of glucocorticoid inhibition of cox activity, prostanoid synthesis and mitogen-induced prostaglandins production suggested the existence of another enzyme (6). The discovery of the second cox gene (cox-2) occurred after the examination of gene expression in chicken embryo cells transformed with RNA tumor viruses (7). The human gene was subsequently cloned (8) showing a substantially smaller gene size of approximately 8 kb (9), but similar to cox-1 exon-intron structure (10). The comparison of cox-1 and cox-2 protein structures reveals 64% overall amino acid identity between enzymes. However, the cox-1 protein contain a short sequence (17 amino acids) at amino terminus that is not present in the cox-2 protein (11) and cox-2 contains another sequence (18 amino acids) at carboxyl terminus that is not present in the cox-1 protein. In spite of structural similarities, there are differences between both enzymes in substrate and inhibitor selectivity, e.g., cox-2 accepts a wider range of fatty acids as substrates than cox-1 (4). Moreover, cox-2 is present on the nuclear membrane and the endoplasmic reticulum (ER), while cox-1 is found only on the ER membranes (12). Cox-1 protein and mRNA was detected in virtually all mammalian tissues (5) and cox-2 mRNA was detected in all examined tissues (14). The constitutive form of the enzyme is now termed cox-1 and the inducible form is called cox-2. The induction of cox-2 gene occurs in response to growth factors, oncogene expression, depolarization in neurons, in hormonal response in osteoblasts, mesangial and granulosa cells, and in inflammatory response in macrophages, neutrophils, epithelial and endothelial cells, synoviocytes, chondrocytes, mast and amnion cells (13, 18). However, cox-2 is constitutively expressed in neurons and gastric mucosa (14, 22). The cox-1 and cox-2 enzymes are respectively called physiological and pathological because most of the stimulatory processes that induce cox-2, are associated with inflammation like bacterial lipopolysaccharide, interleukin-1 and tumor necrosis factor alpha, while cox-1 expression is important in cytoprotection and maintaining physiological functions. The corticosteroids and anti-inflammatory interleukins decrease cox-2 activity (13,15). Most conventional nonsteroidal anti-inflammatory drugs (NSAIDs) inhibit cox activity by acetylation of Ser-530 located near the active site, preventing the entrance of substrate AA and its contact with the Tyr-385 active site (20, 21). Moreover, NSAIDs side-effects like gastrointestinal bleeding and renal dysfunction are considered to be caused by the inhibition of cox-1 physiological functions (23). The gene knockout experiments in mice show that cox-1 gene disruption caused platelets unresponsiveness to AA, no gastric or intestinal bleeding nor any renal pathology but reduction of fetus survival (28). The cox-2 knockout strain shows unchanged response to inflammation, but on the other hand infertility due to the lack of ovulation and massive renal developmental deficiencies (29, 30). Prostanoids play important role in human physiology, which is demonstrated by biological and pharmaceutical significance of cox inhibitors. They mediate a variety of intra- and extracellular interactions including homeostasis, bone development, glomerular filtration and water balance, bronchodilatory respiratory function, cryoprotective gastric function, ovulation, fertilization, embryo implantation and development, labor initiation, modulation of immunological responses, sleep and other processes in central nervous system. Prostaglandins show both vasodilatory and venule vasoconstrictory activities.

Cox-1 is the only form detectable in platelets responsible for AA-induced platelets aggregation. Inhibition of cox-1 leads to decreased production of thromboxane A2 in platelets and prostacyclin in endothelial cells. However, cox-1 activity regenerates in endothelial cells and prostacyclin production is reestablished. This effect provides grounds for prophylaxis against thromboembolic disease (16). The cytoprotective role of prostanoids in the stomach and intestine is mostly due to their vasodilating abilities causing increased mucosal blood flow and preserving the integrity of mucosal epithelium (19).

High level of Cox-2 is associated with active gastritis caused by bacterium *Helicobacter pylori* (39). It seem that cox-1 is predominant generator of protective gastric mucosal prostaglandins even with *Helicobacter pylori* infection raising the possibility of therapeutic selective cox-2 inhibition.

Epidemiological studies showed that chronic intake of NSAIDs decreases the incidence of colon and breast cancers and a 50% reduction in mortality in patients with colorectal cancer (41,42). Similar effect during treatment was observed in young patients with familiar adenomatous polyposis, a pathological condition in which colorectal polyps develop spontaneously and progress to tumors (43). Human breast tumors and colorectal adenomas and adenocarcinomas express higher levels of cox-2 gene and protein than surrounding normal tissues (44,45), providing an attractive therapeutic target.

Similar epidemiological studies showed the correlation between cox enzymes, prostaglandin production and Alzheimer's disease (AD), Parkinson's disease and other neurogenerative diseases. AD is a progressive dementing illness characterized by pathological features like neuritic amyloid plaques, neurofibrillary tangles, loss of neuronal cells and synapses and increased gliosis. Several studies disclosed 50% reduced risk for AD in individuals taking NSAIDs (46,47) and reduced severity and incidence of AD (48). Inflammatory events like increased expression of proinflammatory cytokines such as interleukin-1 and tumor necrosis factor alpha, intracellular adhesion molecule ICAM-1, complement cascade and acute phase protein alpha-1 antichymotrypsin all are present in AD (49, 50, 51, 52). Cox-2 but not cox-1 mRNA expression is elevated in cerebral cortex and hippocampal formation of AD brain and cox-2 protein content correlates with the amount of amyloid plaques (53). A major therapeutic benefit of the new selective cox-2 inhibitors can lead to delaying or preventing AD in subject genetically at risk. Inflammation contributes also to ischemic stroke and cox-2 increased expression is present after stroke in damage neurons causing accelerated apoptotic death. The reduced expression of cox-2 by drugs inhibiting microglial activation after stroke is associated with increased neuronal survival (54).

Recent finding suggest that cox-2 is a major source of systemic prostacyclin synthesis in healthy subjects (61). The increased production of prostacyclin is observed in patients with signs of platelets activation such as unstable angina, severe atherosclerosis and during angioplasty (62, 63, 64).

SUMMARY OF THE INVENTION

This invention relates to antisense oligonucleotides that bind to polynucleotides encoding COX-2, thus preventing production of a COX-2 polypeptide. The present invention provides antisense oligonucleotides that inhibit COX-2 expression, and use thereof to reduce activity of COX-2 in tissues, in order to treat diseases such as rheumatoid arthritis, inflammatory bowel disease, multiple sclerosis, chronic liver disease, ulcerative colitis, cell proliferative disorders and inflammation associated with Alzheimer's Disease and stroke. The invention features use of antisense oligonucleotides to treat such diseases by inhibiting the synthesis of COX-2 and preventing the recruitment and activation of macrophages.

The invention features antisense oligonucleotide molecules that specifically bind polynucleotides encoding COX-2. In a preferred embodiment the antisense oligonucleotides bind mRNA or precursor mRNA encoding COX-2. In another embodiment, the antisense oligonucleotides are about 8 to about 30 nucleic acids in length and can be either DNA or RNA. However, other lengths including, for example, about 8 to 11 and about 21 to 30 nucleotides are also contemplated by the present invention. The antisense oligonucleotides may be chemically modified. In another embodiment, they oligonucleotides of the present invention have mixed backbones (e.g., partially phosphodiester and partially phophorothioate) or chimeric structures (e.g., sugar modified bases and backbone modifications).

In another embodiment, the invention features a method for suppressing COX-2 production in a cell by administering to the cell an amount of antisense oligonucleotide molecules sufficient to specifically bind polynucleotides encoding COX-2, thereby suppressing COX-2 levels. In another aspect, the invention features a method for treating a subject having or at risk of having an COX-2-associated disorder, by administering to the subject an effective amount of antisense oligonucleotide which specifically binds mRNA or precursor-mRNA encoding COX-2. The COX-2 disorder may be an inflammatory disorder, for example. In a particular embodiment, the disorder is rheumatoid arthritis.

In still another aspect, the invention provides a pharmaceutical composition for treatment of a disorder associated with COX-2. The composition comprises an antisense oligonucleotides of the invention either alone, or in combination with other antisense molecules or pharmaceutical agents.

The invention provides several advantages. For example, the antisense oligonucleotides of the invention are specific for COX-2 polynucleotides. A further advantage of the present invention is that the antisense oligonucleotide molecules can be delivered exogenously or can be expressed from DNA or RNA vectors that are delivered to specific cells. In a preferred embodiment the antisense oligonucleotides are provided by transcription of a recombinant DNA sequence. The recombinant DNA sequence may be in a plasmid or viral vector.

In yet another embodiment, a method of monitoring the effectiveness of suppressing COX-2 expression after administering a therapeutically effective amount of the antisense oligonucleotide is provided, the method comprises detecting COX-2 levels before and after the antisense therapy.

Other features and advantages of the invention will be apparent from the following detailed description, and from the claims.

DETAILED DESCRIPTION OF THE INVENTION

The antisense oligonucleotides of the present invention can effectively reduce COX-2 expression and can be used to treat disease associated with COX-2, such as rheumatoid arthritis (RA), inflammatory bowel disease, cirrhosis, multiple sclerosis chronic liver disease, ulcerative colitis, cell proliferative disorders, and inflammation associated with Alzheimer's Disease and stroke. The antisense oligonucleotides can be delivered to cells in culture or to cells or tissues in humans or delivered in animal models having these diseases. Binding of COX-2 by an antisense oligonucleotide of the invention can be used to inhibit inflammatory cell function and/or cell recruitment as well as alleviate disease symptoms.

It has been shown that COX-1 protein and mRNA is detectable in virtually all mammalian tissues (5) and COX-2 mRNA was detected in all examined tissues (14).The constitutive form of the enzyme is now termed COX-1 and the inducible form is called COX-2. The induction of COX-2 gene occurs in response to growth factors, oncogene expression, depolarization in neurons, in hormonal response in osteoblasts, mesangial and granulosa cells, and in inflammatory response in macrophages, neutrophils, epithelial and endothelial cells, synoviocytes, chondrocytes, mast and amnion cells (13, 18). However, COX-2 is constitutively expressed in neurons and gastric mucosa (14, 22). The COX-1 and COX-2 enzymes are respectively called physiological and pathological because most of the stimulatory processes that induce COX-2, are associated with inflammation like bacterial lipopolysaccharide, interleukin-1 and tumor necrosis factor alpha, while COX-1 expression is important in cytoprotection and maintaining physiological functions. The corticosteroids and anti-inflammatory interleukins decrease COX-2 activity (13,15). Most conventional nonsteroidal anti-inflammatory drugs (NSAIDs) inhibit COX activity by acetylation of Ser-530 located near the active site, preventing the entrance of substrate AA and its contact with the Tyr-385 active site (20, 21). Moreover, NSAIDs side-effects like gastrointestinal bleeding and renal dysfunction are considered to be caused by the inhibition of COX-1 physiological functions (23). The gene knockout experiments in mice show that COX-1 gene disruption caused platelets unresponsiveness to AA, no gastric or intestinal bleeding nor any renal pathology but reduction of fetus survival (28). The COX-2 knockout strain shows unchanged response to inflammation, but on the other hand infertility due to the lack of ovulation and massive renal developmental deficiencies (29, 30). Prostanoids play important role in human physiology, which is demonstrated by biological and pharmaceutical significance of COX inhibitors. They mediate a variety of intra- and extracellular interactions including homeostasis, bone development, glomerular filtration and water balance, bronchodilatory respiratory function, cryoprotective gastric function, ovulation, fertilization, embryo implantation and development, labor initiation, modulation of immunological responses, sleep and other processes in central nervous system. Prostaglandins show both vasodilatory and venule vasoconstrictory activities.

COX-1 is the only form detectable in platelets responsible for AA-induced platelets aggregation. Inhibition of COX-1 leads to decreased production of thromboxane A2 in platelets and prostacyclin in endothelial cells. However, COX-1 activity regenerates in endothelial cells and prostacyclin production is reestablished. In contrary, in platelets COX-1 is irreversibly inhibited for their lifetime in the circulation. This effect provides grounds for prophylaxis against thromboembolic disease (16). The cytoprotective role of prostanoids in the stomach and intestine is mostly due to their vasodilating abilities causing increased mucosal blood flow and preserving the integrity of mucosal epithelium (19).

PGs play very important role in gestation and parturition. They induce uterine contractions during labor and indomethacin delays premature labor by inhibiting PGs production (24). Both COX enzymes are expressed in the uterus in early pregnancy contributing to placenta development and ovum implantation (25). Constitutive level of COX-1 in the amnion regulates the maintenance of a healthy pregnancy (26). PGs generated by COX-2 enzyme influence the birth process since its level in placenta and amnion increases immediately before and after the beginning of labor (27).

COX enzymes modulate nerve transmission and central nervous system (CNS) functions. COX-1 is expressed in neurons throughout the brain, but mostly in the forebrain, and COX-2 is constitutively distributed only in cortex, hippocampus, hypothalamus and spinal cord (31). However, COX-2 activity is present in neurons as well as in the nonneuronal cells and is stimulated during normal and abnormal nerve transmission (32). Pain and fever can also be induced by abnormal production of prostanoids and blocked by COX inhibitors (17). COX-2 enzyme is stimulated in response to pyrogens in the endothelium of the blood vessels perfusing the thermoregulatory center in hypothalamus responsible for fever (33). The increase of COX-2 activity in spinal cord during inflammatory injury causes hyperalgesia (34) and the application of COX inhibitors create potent analgesic effect (35).

COX enzymes exert very significant biological effects in many pathophysiological states. PGs level play important role in maintaining blood flow of the compromised kidney in patients with heart failure, liver cirrhosis, renal insufficiency or chronically administered NSAIDs (36). COX-2 expression in kidney appears important in the control of renin release (40). High levels of COX activity is present in synovia from patients with rheumatoid arthritis (RA) in comparison with normal subjects or patients with osteoarthritis (37). Only COX-2 is stimulated by interleukin-1, proinflammatory cytokine which systemic levels correlate with the progression of the disease (38). High level of COX-2 is associated with active gastritis caused by bacterium *Helicobacter pylori* (39). It seems that COX-1 is predominant generator of protective gastric mucosal prostaglandins even with *Helicobacter pylori* infection raising the possibility of therapeutic selective COX-2 inhibition.

Epidemiological studies showed that chronic intake of NSAIDs decreases the incidence of colon and breast cancers and a 50% reduction in mortality in patients with colorectal cancer (41,42). Similar effect during treatment was observed in young patients with familiar adenomatous polyposis, a pathological condition in which colorectal polyps develop spontaneously and progress to tumors (43). Human breast tumors and colorectal adenomas and adenocarcinomas express higher levels of COX-2 gene and protein than surrounding normnal tissues (44,45), providing an attractive therapeutic target.

Similar epidemiological studies showed the correlation between COX enzymes, prostaglandin production and Alzheimer's disease (AD), Parkinson's disease and other neurogenerative diseases. AD is a progressive dementing illness characterized by pathological features like neuritic amyloid plaques, neurofibrillary tangles, loss of neuronal cells and synapses and increased gliosis. Several studies disclosed 50% reduced risk for AD in individuals taking NSAIDs (46,47) and reduced severity and incidence of AD (48). Inflammatory events like increased expression of proinflammatory cytokines such as interleukin-1 and tumor necrosis factor alpha, intracellular adhesion molecule ICAM-1, complement cascade and acute phase protein alpha-1 antichymotrypsin all are present in AD (49, 50, 51, 52). COX-2 but not COX-1 mRNA expression is elevated in cerebral cortex and hippocampal formation of AD brain and COX-2 protein content correlates with the amount of amyloid plaques (53). A major therapeutic benefit of the new selective COX-2 inhibitors can lead to delaying or preventing AD in subjects genetically at risk. Inflammation contributes also to ischemic stroke and COX-2 increased expression is present after stroke in damage neurons causing accelerated apoptotic death. The reduced expression of COX-2 by drugs inhibiting microglial activation after stroke is associated with increased neuronal survival (54).

Recent finding suggest that COX-2 is a major source of systemic prostacyclin synthesis in healthy subjects (61). The increased production of prostacyclin is observed in patients with signs of platelets activation such as unstable angina, severe atherosclerosis and during angioplasty (62, 63, 64).

"Antisense oligonucleotide" means any RNA or DNA molecule which can bind specifically with a targeted polynucleotide sequence, interrupting the expression of that gene's protein product. The antisense molecule binds to either the messenger RNA forming a double stranded molecule which cannot be translated by the cell or to the DNA or other polynucleotide encoding COX-2. Antisense oligonucleotides of the present invention include oligonucleotides of about 8 to 30 nucleotides and more preferably about 8–11 or 21–30 nucleotides in length.

In another embodiment, the antisense oligonucleotides of the present invention have chemical modifications in the phosphodiester backbone and in the sugar. These chimeric oligonucleotides contain mixed backbones. In another embodiment, the oligonucleotides are conjugated directly or via a linker molecule to a polymer, peptide or sugar (e.g., glucose).

In the cell, the antisense oligonucleotides hybridize to the corresponding target polynucleotide, forming a double-stranded or triplex molecule. The antisense oligonucleotides interfere with the translation of, for example, mRNA, since the cell will not translate a mRNA that is double-stranded. Antisense oligomers of about 8 to 30 nucleotides are preferred, since they are easily synthesized and are less likely to cause problems than larger molecules when introduced into the target COX-2 producing cell.

Use of a oligonucleotides to stall transcription is known as the triplex strategy since the oligomer winds around double-helical DNA, forming a three-strand helix. Therefore, these triplex compounds can be designed to recognize a unique site on a chosen gene (Maher, et al., 1991, *Antisense Res. and Dev.*, 1(3 ):227; Helene, C., 1991, *Anticancer Drug Design*, 6(6):569).

These and other uses of antisense methods to inhibit the in vivo transcription or translation of genes are well known in the art (e.g., De Mesmaeker, et al., 1995. Backbone modifications in oligonucleotides and peptide nucleic acid systems. *Curr. Opin. Struct. Biol.* 5:343–355; Gewirtz, A. M., et al., 1996b. Facilitating delivery of antisense oligodeoxynucleotides: Helping antisense deliver on its promise; *Proc. Natl. Acad. Sci. U.S.A.* 93:3161–3163; Stein, C. A. A discussion of G-tetrads 1996. Exploiting the potential of antisense: beyond phosphorothioate oligodeoxynucleotides. *Chem. and Biol.* 3:319–323).

As used herein, the term "nucleic acid," "polynucleotide," "oligonucleotide" or "nucleic acid sequence" refers to a polymer of deoxyribonucleotides or ribonucleotides, in the form of a separate fragment or as a component of a larger construct. For example, nucleic acids can be assembled from cDNA fragments or from polynucleotides to generate a synthetic gene which is capable of being expressed in a recombinant transcriptional unit. Oligonucleotide or nucleic acid sequences of the invention include DNA, RNA, and cDNA sequences.

A "promoter" is a minimal DNA sequence sufficient to direct transcription of a DNA sequence to which it is operably linked. A "promoter" also includes promoter elements sufficient for promoter-dependent gene expression controllable for cell-type specific expression, tissue-specific expression, or inducible by external signals or agents; such elements may be located in the 5' or 3' regions of the native gene.

The term "operably associated" refers to functional linkage between the regulatory (e.g. promoter) sequence and the nucleic acid regulated by the regulatory sequence. The operably linked regulatory sequence controls the expression of the product. The regulatory sequence may be heterologous to the desired gene sequence.

A "vector" is any compound or formulation, biological or chemical, that facilitates transformation or transfection of a target cell with a polynucleotide of interest, for example antisense oligonucleotides. Exemplary biological vectors include viruses, particularly attenuated and/or replication-deficient viruses. Exemplary chemical vectors include lipid complexes and DNA constructs.

To "inhibit" or "inhibiting" activity is to reduce that activity a measurable amount, preferably a reduction of at least 30% or more. Where there are multiple different activities that may be inhibited (for example, antisense molecules that bind polynucleotides encoding COX-2 may have the ability to reduce expression of the COX-2 protein, the recruitment of macrophages, and may also have the ability to decrease T cell proliferation), the reduction of any single activity (with or without the other activities) is sufficient to fall within the scope of this definition.

To "specifically bind" is to preferably hybridize to a particular polynucleotide species. The specificity of the hybridization can be modified and determined by standard molecular assays known to those skilled in the art.

A "suppressive-effective" amount is that amount of the construct, and thus antisense, administered in an amount sufficient to suppress the expression of the target, e.g., inhibit translation of mRNA, by at least 75% of the normal expression, and preferably by at least 90%. The effectiveness of the construct can be determined phenotypically or by standard Northern blot analysis or immunohistochemically, for example. Other standard nucleic acid detection techniques or alternatively immunodiagnostic techniques will be known to those of skill in the art (e.g., Western or Northwestern blot analysis).

A "transgenic animal" is an animal that includes a transgene that is inserted into an embryonal cell and becomes a part of the genome of the animal which develops from that cell, or an offspring of such an animal. In the transgenic animals described herein, the transgene causes specific tissue cells to express an antisense oligonucleotide which specifically binds COX-2 polynucleotide. Any animal that can be produced by transgenic technology is included in the invention, although mammals are preferred. Preferred mammals include non-human primates, sheep, goats, horses, cattle, pigs, rabbits, and rodents such as guinea pigs, hamsters, rats, gerbils, and mice.

A "transgene" is a DNA sequence that includes one or more selected DNAs, e.g., encoding antisense oligonucleotides that bind mRNA encoding COX-2, to be expressed in a transgenic animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected DNA, all operably linked to the selected DNA, and may include an enhancer sequence.

A "disorder associated with COX-2" or "disease associated with COX-2" is any disease state associated with the expression of COX-2. An example of such disorders include rheumatoid arthritis, inflammatory bowel disease, cirrhosis, multiple sclerosis, chronic liver disease, ulcerative colitis, cell proliferative disorders, and inflammation associated with Alzheimer's Disease and stroke.

Antisense Oligonucleotides

The present invention provides a method for ameliorating or inhibiting the production of COX-2 in diseases associated with COX-2 production. Inhibition of COX-2 production is achieved by administering to the cell, tissue or subject an antisense oligonucleotide sequence which is capable of hybridizing to the nucleic acid sequence of an COX-2 polynucleotide. This antisense oligonucleotide inhibits, or down regulates the expression of the COX-2 gene product in the cell, tissue or subject.

The invention additionally provides antisense oligonucleotides which reduce expression of COX-2. An antisense oligonucleotide of the invention has a sequence that is complementary to, and thus hybridizes with the nucleic acid sequence of the target COX-2 polynucleotide. However, absolute complementarity is not required. The polynucleotide sequence of the target COX-2 sequence can be either a DNA or an RNA sequence. The target includes sequences upstream from the 5' terminus of the structural gene, such as regulatory sequences, and sequences downstream from the 3' terminus of the structural gene, as well as sequences of the coding region of the gene or mRNA. An antisense oligonucleotide is "complementary" to the target COX-2 oligonucleotide, and thus useful according the invention, if it is capable of forming a stable duplex or triplex with, at least part of, the target polynucleotide sequence of the target so that processing, transcription or translation of the polynucleotides is inhibited, or capable of forming a complex, such as a triplex, with genomic DNA of the gene so that promotion of transcription is inhibited or premature transcript termination is produced. (Green et al., 1990 *Clinical Biotechnology*, 2:75). When the antisense molecule hybridizes to the target polynucleotide, stable duplex or triplex formation depends on the sequence and length of the hybridizing polynucleotide and the degree of complementarity between the antisense molecule and the target sequence. The system can tolerate less fidelity (complementarity) when a longer oligonucleotide is used. However, oligonucleotides of about 8 to about 30 bases in length and having sufficient complementarity to form a duplex having a melting temperature of greater than about 40° C. under physiological conditions are particularly well suited for practice of the invention (Thoung, et al., 1987 *PNAS USA*, 84:5129; Wilson et al., 1988 *Nucleic Acids Res.*, 16:5137; Maniatis, et al., *Molecular Cloning: A Laboratory Manual*, Old Spring Harbor Laboratory Press, Cold Spring Harbor, N.Y., 1982). Accordingly, such oligonucleotides are preferred.

The antisense molecules of the invention have a specific substrate binding portion which is complementary to a target region of COX-2 polynucleotides, and have nucleotide sequences within or surrounding the substrate binding site which impart the ability to selectively hybridize to relative portions of the COX-2 polynucleotide. Ninety-two illustrated target binding sequences, corresponding to antisense molecules having SEQ ID NOs:1–92 are provided and described herein. These exemplary antisense molecules were designed to hybridize to various sites on the COX-2 mRNA or DNA. Such COX-2 sequences are readily identifiable in the art (see, for example, Table 1, below).

TABLE 1

| Sequence | GenBak Accession # | cDNA length | Coding Sequence | 5' UTR Length | 3' UTR Length |
|---|---|---|---|---|---|
| mCOX-2 | M64291 | 3986 | 125–1939 | 1–124 | 1940–3986 |
| hCOX-2 | M90100 | 3387 | 98–1912 | 1–97 | 1913-3387 |

The invention includes antisense oligonucleotides which hybridize with a polynucleotide sequence comprising a COX-2 sequence (see Table 1) or its complement. The antisense oligonucleotides employed may be unmodified or modified RNA or DNA molecules. Suitable modifications include, but are not limited to, the ethyl or methyl phosphonate modification disclosed in U.S. Pat. No. 4,469,863, the disclosure of which is incorporated by reference, and the phosphorthioate modifications to deoxynucleotides described by LaPlanche, et al., 1986 *Nucleic Acids Research*, 14:9081, and by Stec, et al., 1984 *J. Am. Chem Soc.* 106:6077. The modification to the antisense oligonucleotides is preferably a terminal modification in the 5' or 3' region. Preferred are modifications of the 3' terminal region. Also preferred are modifications with methyl groups added to 5' carbon atoms as described by Saha, et al., 1993 *CEN*, 44:44. Alternatively, the antisense molecules can have chimeric backbones of two or more modified nucleic acid bases, which are modified by different methods. Such methods include, for example, amino acid or nucleic acid modification as described by K. Ramasamy and W. Seifert (Bioorganic & Medicinal Chemistry Letters, 6(15): 1799–1804 (1996)) or 4' sugar substituted olignucleotides described by G. Wang and W. Seifert (Tetrahedron Letters, 37(36):6515–6518 (1996)).

Phosphodiester-linked oligonucleotides are particularly susceptible to the action of nucleases in serum or inside cells, and therefore in a preferred embodiment the antisense molecules of the present invention are phosphorothioate or methyl phosphonate-linked analogues, which have been shown to be nuclease-resistant. Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2NHOCH_2$, $CH_2N(CH_3)OCH_2$, $CH_2ON(CH_3)CH_2$, $CH_2N(CH_3)N(CH_3)CH_2$ and $ON(CH_3)$ $CH_2CH_2$ backbones (where phosphodiester is $OPOCH_2$). Also preferred are oligonucleotides having morpholino backbone structures (Summerton, J. E. and Weller, D. D., U.S. Pat. No. 5,034,506). In other preferred embodiments, 2'-methylribonucleotides (Inoue, et al., 1987 *Nucleic Acids Research*, 15:6131) and chimeric oligonucleotides that are composite RNA-DNA analogues (Inoue, et al., 1987 *FEBS Lett.*, 215:327) may also be used for the purposes described herein. Finally, DNA analogues, such as peptide nucleic acids (PNA) are also included (Egholm, et al., 1993 *Nature* 365:566; P. E. Nielsen, M. Egholm, R. H. Berg, O. Buchardt, 1991 *Science*, 254:1497) and can be used according to the invention. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)nCH_3$, $O(CH_2)nNH_2$ or $O(CH_2)$ nCH3 where n is from 1 to about 10; C1 to C10 lower alkyl, substituted lower alkyl, alkaryl or aralkyl; Cl; Br; CN; $CF_3$; $OCF_3$; O, S, or N-alkyl; O, S or N alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of a oligonucleotide; or a group for improving the pharmacodynamic properties of a oligonucleotide and other substituents having similar properties. Oligonucleotides may also have sugar mimetics such as cyclobutyls in place of the pentofuranosyl group. Other preferred embodiments may include at least one modified base form or "universal base" such as inosine. The preparation of base-modified nucleosides, and the synthesis of modified oligonucleotides using said base-modified nucleosides as precursors, has been described, for example, in U.S. Pat. Nos. 4,948,882 and 5,093,232. These base-modified nucleosides have been designed so that they can be incorporated by chemical synthesis into either terminal or internal positions of a oligonucleotide. Such base-modified nucleosides, present at either terminal or internal positions of a oligonucleotide, can serve as sites for attachment of a peptide or other antigen. Nucleosides modified in their sugar moiety have also been described (e.g., U.S. Pat. No. 5,118, 802 and U.S. Pat. No. 5,681,940, both of which are incorporated by reference) and can be used similarly. Persons of ordinary skill in this art will be able to select other linkages for use in the invention. These modifications also may be designed to improve the cellular uptake and stability of the oligonucleotides. It is understood that depending on the route or form of administration of the antisense oligonucleotides of the invention, the modification or site of modification will vary (e.g., 5' or 3' modification). One of skill in the art could readily determine the appropriate modification without undue experimentation.

In order for the target cell, tissue or subject to be rendered susceptible to the antisense oligonucleotides in accordance with the method of the invention, the cells must be exposed to the oligonucleotide under condition that facilitate their uptake by the cell, tissue or subject. In vitro therapy may be accomplished by a number of procedures, including, for example, simple incubation of the cells or tissue with the oligonucleotide in a suitable nutrient medium for a period of time suitable to inhibit COX-2 production.

The antisense oligonucleotides of the invention can be delivered alone or in conjunction with other agents such as immunosuppressive drugs, ribozymes or other antisense molecules. For example, ribozymes or antisense molecules that specifically bind mRNA encoding another cytokine, such as TNF-α or interferon-γ, can be used with the antisense molecules of the present invention. Further, combinations of the antisense molecules of the invention, e.g., SEQ ID NO:1–92, can be used. Agents useful in treating rheumatoid arthritis, such as colloidal gold or methotrexate, may also be used in conjunction with the antisense molecules which specifically bind COX-2. Anti-inflammatory agents, such as non-steroidal anti-inflammatory drugs, corticosteroids, and hydroxychloroquine, immunosuppressive agents such as cyclosporine, and cytotoxic drugs such as cyclophosphamide, azathioprine, may also be used in conjunction with the antisense molecules of the invention.

Additionally, the antisense oligonucleotides of the present invention may be administered ex vivo by harvesting cells or tissue from a subject, treating them with the antisense oligonucleotide, then returning the treated cells or tissue to the subject. The present invention provides method for the treatment of a disease which is associated with COX-2. Such therapy would achieve its therapeutic effect by introduction of the appropriate antisense oligonucleotide which binds polynucleotides encoding COX-2 into cells of subjects having the disorder. Delivery of the COX-2 antisense molecule can be achieved using a recombinant expression vector such as a chimeric virus or a colloidal dispersion system. Many of the methods as described herein can be performed in vivo or ex vivo. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sequence encoding an antisense oligonucleotide which specifically binds polynucleotides encoding COX-2 into the viral vector, along with another gene which encodes the ligand for a receptor on a specific target cell, for example, the vector is now target specific. Preferred targeting is accomplished by using an antibody to target the retroviral vector. Those of skill in the art will know of, or can readily ascertain without undue experimentation, specific polynucleotide sequences which can be inserted into the retroviral genome, for example, to allow target specific delivery of the retroviral vector containing the antisense oligonucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to Ψ2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for antisense oligonucleotides that bind polynucleotides encoding COX-2 is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., 1981 *Trends Biochem. Sci.*, 6:77). In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., 1988 *Biotechniques*, 6:682).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest which will bind to another compound, such as a receptor.

Another delivery system for the antisense oligonucleotides of the invention at particular sites in a subject, for instance at a joint site afflicted with rheumatoid arthritis, includes the use of gene-activated matrices. In this system the antisense molecule is coated on a biocompatible matrix, sponge or scaffold and implanted at the tissue site wherein cells proliferate and grow on the scaffold, taking up the antisense oligonucleotide (See for example U.S. Pat. No. 5,763,416, which is incorporated herein by reference).

In yet another delivery system, the antisense molecules of the invention may be microinjected into cells. The antisense molecules may be prepared in an appropriate buffer and the naked oligonucleotide, either alone or contained in an appropriate vector, microinjected, for example, into a stem cell of a tissue to be treated.

In addition, antisense oligonucleotides according to the invention may also be administered in vivo. Antisense oligonucleotides can be administered as the compound or as a pharmaceutically acceptable salt of the compound, alone or in combination with pharmaceutically acceptable carriers, diluents, simple buffers, and vehicles. For example expression vectors that produce antisense molecules can be engineered from DNA duplexes in the laboratory and introduced into cells (Weintraub, et al., 1990 *Sci. Amer.* 1:40). Most preferably, antisense oligonucleotides are mixed individually or in combination with pharmaceutically acceptable carriers to form compositions which allow for easy dosage preparation.

An antisense oligonucleotide of the invention can be administered to provide in vivo therapy to a subject having a disorder which is associate with COX-2 expression. Such therapy can be accomplished by administering ex vivo and in vivo as the case may be, a therapeutically effective amount of antisense oligonucleotide. The term "therapeutically effective" means that the amount of antisense oligonucleotide administered is of sufficient quantity to suppress, to some beneficial degree, expression of COX-2.

Antisense oligonucleotide according to the present invention can be administered to the patient in any acceptable manner including orally, by injection, using an implant, nasally and the like. Oral administration includes administering an oligonucleotide of the present invention in tablets, suspension, implants, solutions, emulsions, capsules, powders, syrups, water composition, and the like. Nasal administration includes administering the composition of the present invention in sprays, solutions and the like. Injections and implants are preferred because they permit precise control of the timing and dosage levels useful for administration, with injections being most preferred. Antisense oligonucleotides are preferably administered parenterally.

The therapeutic agents useful in the method of the invention can be administered parenterally by injection or by gradual perfusion over time. Administration may be intravenously, intraperitoneally, intramuscularly, subcutaneously, intra-cavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

The invention also includes a composition for therapy comprising an effective amount of an enzymatic RNA of the invention or combination thereof, and a physiologically acceptable excipient or carrier.

Physiologically acceptable and pharmaceutically acceptable excipients and carriers are well known to those of skill in the art. By "physiologically or pharmaceutically acceptable carrier" as used herein is meant any substantially non-toxic carrier for administration in which an antisense oligonucleotide of the invention will remain stable and bioavailable when used. For example, the antisense oligonucleotide of the invention can be dissolved in a liquid, dispersed or emulsified in a medium in a conventional manner to form a liquid preparation or is mixed with a semi-solid (gel) or solid carrier to form a paste, ointment, cream, lotion or the like.

Suitable carriers include water, petroleum jelly (vaseline), petrolatum, mineral oil, vegetable oil, animal oil, organic and inorganic waxes, such as microcrystalline, paraffin and ozocerite wax, natural polymers, such as xanthanes, gelatin, cellulose, or gum arabic, synthetic polymers, such as discussed below, alcohols, polyols, water and the like. Preferably, because of its non-toxic properties, the carrier is a water miscible carrier composition that is substantially miscible in water. Such water miscible carrier composition can include those made with one or more ingredients set forth above but can also include sustained or delayed release carrier, including water containing, water dispersable or water soluble compositions, such as liposomes, microsponges, microspheres or microcapsules, aqueous base ointments, water-in-oil or oil-in-water emulsions or gels.

The carrier can comprise a sustained release or delayed release carrier. The carrier is any material capable of sustained or delayed release of the antisense molecule specifically directed against COX-2 polynucleotide to provide a more efficient administration resulting in one or more of less frequent and/or decreased dosage of the antisense molecule, ease of handling, and extended or delayed effects. The carrier is capable of releasing the oligomer when exposed to the environment of the area for diagnosis or treatment or by diffusing or by release dependent on the degree of loading of the oligonucleotide to the carrier in order to obtain release of the antisense oligonucleotide of the invention. Non-limiting examples of such carriers include liposomes, microsponges, microspheres, gene-activated matrices, as described above, or microcapsules of natural and synthetic polymers and the like. Examples of suitable carriers for sustained or delayed release in a moist environment include gelatin, gum arabic, xanthane polymers; by degree of loading include lignin polymers and the like; by oily, fatty or waxy environment include thermoplastic or flexible thermoset resin or elastomer including thermoplastic resins such as polyvinyl halides, polyvinyl esters, polyvinylidene halides and halogenated polyolefins, elastomers such as brasiliensis, polydienes, and halogenated natural and synthetic rubbers, and flexible thermoset resins such as polyurethanes, epoxy resins and the like.

Preferably, the sustained or delayed release carrier is a liposome, microsponge, microsphere or gel.

The compositions of the invention are administered by any suitable means, including injection, implantation, transdermal, intraocular, transmucosal, bucal, intrapulmonary, and oral.

Preferably the carrier is a pH balanced buffered aqueous solution for injection. However, the preferred carrier will vary with the mode of administration.

The compositions for administration usually contain from about 0.0001% to about 90% by weight of the antisense oligonucleotide of the invention compared to the total weight of the composition, preferably from about 0.5% to about 20% by weight of the antisense oligonucleotide of the invention compared to the total composition, and especially from about 2% to about 20% by weight of the antisense oligonucleotide of the invention compared to the total composition.

The effective amount of the antisense oligonucleotide of the invention used for therapy or diagnosis of course can vary depending on one or more of factors such as the age and weight of the patient, the type of formulation and carrier ingredients, frequency of use, the type of therapy or diagnosis preformed and the like. It is a simple matter for those of skill in the art to determine the precise amounts to use taking into consideration these factors and the present specification.

Transgenic Animals

In a further embodiment, a transgenic animal can be developed using a construct containing the antisense oligonucleotide and method of the invention in order to identify the impact of increased or decreased COX-2 levels on a particular pathway or phenotype. The construct can be any number of vectors containing the antisense oligonucleotide of the invention. Protocols useful in producing such transgenic animals are described below. The protocol generally follows conventional techniques for introduction of expressible transgenes into mammals. Those of ordinary skill in the art will be familiar with these applications and will be able to apply the techniques in the context of the present invention without undue experimentation.

For example, embryonic target cells at various developmental stages can be used to introduce transgenes encoding an COX-2 antisense molecule. Different methods are used depending on the stage of development of the embryonic target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al., 1985, *Proc. Natl. Acad. Sci. USA* 82:4438–4442). As a consequence, all cells of the transgenic non-human animal will carry the incorporated transgene. In general, this will also be reflected in the efficient transmission of the transgene to offspring of the founder since 50% of the germ cells will harbor the transgene. Microinjection of zygotes is a suitable method for incorporating transgenes in practicing the invention.

Retroviral infection can also be used to introduce a transgene encoding an antisense oligonucleotide which specifically binds COX-2 polynucleotides into a non-human animal. The developing non-human embryo can be cultured in vitro to the blastocyst stage. During this time, the blastomeres can be targets for retroviral infection (Jaenisch, 1976, *Proc. Natl. Acad. Sci. USA* 73:1260–1264). Efficient infection of the blastomeres is obtained by enzymatic treatment to remove the zona pellucida (Hogan, et al., 1986, *Manipulating the Mouse Embryo*, Cold Spring Harbor Laboratory Press, Cold Spring Harbor, N.Y.). The viral vector system used to introduce the transgene encoding an antisense oligonucleotide which specifically binds COX-2 polynucleotides is typically a replication-defective retrovirus carrying the transgene (Jahner, et al., 1985, *Proc. Natl. Acad. Sci. USA* 82:6927–6931; Van der Putten, et al., *Proc Natl. Acad. Sci. USA* 82:6148–6152). Transfection is easily and efficiently obtained by culturing the blastomeres on a monolayer of virus-producing cells (Van der Putten, supra; Steward, et al., 1987, *EMBO J.*, 6:383–388).

Alternatively, infection can be performed at a later stage. Virus or virus-producing cells can be injected into the blastocoele (Jahner, et al., 1982, *Nature*, 298:623–628). Most of the founder animals will be mosaic for the transgene since incorporation occurs only in a subset of the cells which formed the transgenic non-human animal. Further, the founder animals may contain various retroviral insertions of the transgene at different positions in the genome which generally will segregate in the offspring. In addition, it is also possible to introduce transgenes encoding an COX-2 antisense oligonucleotide into the germ line, albeit with low efficiency, by intrauterine retroviral infection of the midgestation embryo (Jahner, et al., supra, 1982).

A third type of target cell for introduction of heterologous nucleic acid sequences is the embryonal stem cell (ES). ES cells are obtained from pre-implantation embryos cultured in vitro and fused with embryos (Evans, et al., 1981, *Nature*, 292:154–156; Bradley, et al., 1984, *Nature*, 309:255–258,; Gossler, et al., 1986, *Proc. Natl. Acad. Sci. USA*, 83:9065–9069; and Robertson, et al., 1986, *Nature*, 322:445–448). Transgenes encoding antisense oligonucleotides which specifically bind COX-2 polynucleotides can be efficiently introduced into the ES cells by DNA transfection or by retro-virus-mediated transduction. These transformed ES cells can thereafter be combined with blastocysts from a non-human animal. The ES cells will thereafter colonize the embryo and contribute to the germ line of the resulting chimeric animal (see for review, Jaenisch, 1988,

*Science*, 240:1468–1474). Any ES cell may be used is accordance with the present invention. It is, however, preferred to use primary isolates of ES cells. Such isolates may be obtained directly from embryos such as with the CCE cell line disclosed by Robertson, E. J., in Current Communications in Molecular Biology, Capecchi, M. R. (Ed.) Cold Springs Harbor Press, Cold Springs Harbor, N.Y. (1989), pp.39–44, or from the clonal isolation of ES cells from the CCE cell line (Scwartzberg, P. A. et al., 1989, *Science* 246:799). ES cells may be derived or isolated from any species, although cells derived or isolated from mammals such as rodents, rabbits, and is non-human primates are preferred.

The cre/lox system as described in U.S. Pat. No. 4,959,317, incorporated herein by reference, can be utilized in the production of transgenic animals. A first and second loxP DNA sequence is introduced into cells connected by a preselected antisense or replacement gene, such as an antisense oligonucleotide which specifically binds COX-2 polynucleotides, herein referred to as a "target transgene". The "target transgene" of interest can be a complete gene or any other sequence of nucleotides including those of homologous, heterologous, or synthetic origin. The target transgene sequence can be for example, an antisense or replacement gene for a structural protein, an enzyme, a regulatory molecule, or an enzyme such as COX-2. The target transgene may also be a gene of undetermined function. Using tissue-specific or developmentally-specific regulatory sequences (as described above) to direct expression of the target transgene, a function could be identified. If the first and second lox sites have the same orientation (direct repeats), activation of the regulatory nucleotide sequence of the transactivator transgene results in a deletion of the target transgene DNA, such that ablation or modification of activity results. If the first and second lox sites have opposite orientation (inverted repeats), activation of the regulatory nucleotide produces an inversion of the nucleotide sequence of the target transgene.

The construct of the invention may be used to introduce DNA sequences into the germ line cells of "non-humans" to create transgenic animals. Mice are useful as transgenic animals. However, other non-humans of the invention include but are not limited to other rodents (e.g., rat, hamster), rabbits, chickens, sheep, goats, pigs, cattle, and non-human primates.

Accordingly, in view of the foregoing, the following antisense sequences are contemplated for use and as compositions in the present invention.

```
5' AAGGATTTGCTGTATGGCTGA      (SEQ ID NO:1)
5' ACAGCAAGGATTTGCTGTATG      (SEQ ID NO:2)
5' CACACTCATACATACACCTCG      (SEQ ID NO:3)
5' GCACTTATACTGGTCAAATCC      (SEQ ID NO:4)
5' GGTACAATCGCACTTATCTG       (SEQ ID NO:5)
5' CTTTGCTGTCTGAG             (SEQ ID NO:6)
5' GGTAGGCTTTGCTGTCTGAGG      (SEQ ID NO:7)
5' GCTGCTGAGGAGTTCCTGGAC      (SEQ JD NO:8)
5' CTGGCTGTGGAGCTGAAGGAG      (SEQ ID NO:9)
5' CAGTTTTCTCCATAGAATCCT      (SEQ ID NO:10)
```

-continued
```
5' TTTTATTCTTGTCAAAAATTCC     (SEQ JD NO:11)
5' GGTTTCAGAAATAATTTTATTC     (SEQ ID NO:12)
5' TATGTAGTGCACTGTGTTTGG      (SEQ ID NO:13)
5' CCCTTGAAGTGGG              (SEQ ID NO:14)
5' GAATGTTATTCACAACGTTCC      (SEQ ID NO:15)
5' CTCATAATTGCATTTCGAAGG      (SEQ ID NO:16)
5' ATGTGATCTGGATGTCAACACA     (SEQ ID NO:17)
5' TAGTCAGCATTGTAAGTTGGTG     (SEQ ID NO:18)
5' AATAGGAGAGGTTAGAGAAGG      (SEQ ID NO:19)
5' CACAATCTCATTTGAATCAGG      (SEQ ID NO:20)
5' GATGAACTTTCTTCTTAGAAG      (SEQ ID NO:21)
5' TCGCTTATGATCTGTCTTGAA      (SEQ ID NO:22)
5' GTAAATATGATTTAAGTCCAC      (SEQ ID NO:23)
5' CTGTCTAGCCAGAGTTTCACC      (SEQ ID NO:24)
5' TCATTTTTCCATCCTTGAAAA      (SEQ ID NO:25)
5' CCATCAATTATCTGATATTTG      (SEQ ID NO:26)
5' GAGGATACATCTCTCCATCA       (SEQ ID NO:27)
5' CCTGAGTATCTTTGACTGTGG      (SEQ ID NO:28)
5' AGGAGGGTAGATCATCTCTGC      (SEQ ID NO:29)
5' GCAAACCGTAGATGCTCAGG       (SEQ ID NO:30)
5' CACCAGACCAAAGACCTCCTG      (SEQ ID NO:31)
5' CAGACCAGGCACC              (SEQ ID NO:32)
5' ATCATCAGACCAGGCACCAGA      (SEQ ID NO:33)
5' CTCAGCCAGATTGTGGCATAC      (SEQ ID NO:34)
5' TCGCATTACTCTGTTGTGTTC      (SEQ ID NO:35)
5' ATGCTCCTGTTTAAGCACATC      (SEQ ID NO:36)
5' CTTGTCTGGAACAACTGCTCA      (SEQ ID NO:37)
5' AGTCTCCTATCAGTATTAG        (SEQ ID NO:38)
5' TGTTGCACATAATCTTCAATC      (SEQ ID NO:39)
5' GTTTGTTGAAAAGTAGTTCTG      (SBQ ID NO:40)
5' AATTGTTTGTTGAAAAGTAGT      (SEQ ID NO:41)
5' GGTGTTAAATTCAGCAGCAAT      (SEQ ID NO:42)
5' TTTCTGGTCATGAATTTGAAA      (SEQ ID NO:43)
5' ATAGAGTTGTTGTAGATAAAC      (SEQ ID NO:44)
5' CTGTTGATAGTTGTATTTCTG      (SEQ ID NO:45)
5' GGTGAATGATTCAACAAACTG      (SEQ ID NO:46)
5' GATACTTTCTGTACTG           (SEQ ID NO:47)
5' CCTGTGATACTTTCTGTACTG      (SEQ ID NO:48)
5' CCTGCTCTGGTCAATGGAAGC      (SEQ ID NO:49)
5' AAAAGACTGGTATTTCATCTG      (SEQ ID NO:50)
```

-continued

| | |
|---|---|
| 5' GTTCTTCAAATGATTCATAGG | (SEQ ID NO:51) |
| 5' TCGATGTCACCATAGAGTGCT | (SEQ ID NO:52) |
| 5' CTTCTACCATGGTTTCACCAA | (SEQ ID NO:53) |
| 5' TGCTCCAACTTCTACCATGGT | (SEQ ID NO:54) |
| 5' GTCCTTTCAAGGAGAATGGTG | (SEQ ID NO:55) |
| 5' CAGTGTTGATGATTTGAAAAC | (SEQ ID NO:56) |
| 5' TGCAGATGAGAGACTGAATTG | (SEQ ID NO:57) |
| 5' GAACACTGAATGAAGTAAAGG | (SEQ ID NO:58) |
| 5' TTTAATGAGCTCTGGATCTG | (SEQ ID NO:59) |
| 5' AACTTGCATTGATGGTGACTG | (SEQ ID NO:60) |
| 5' TGGGATTGATATCATCTAGTC | (SEQ ID NO:61) |
| 5' TACAGTTCAGTCGAACGTTCT | (SEQ ID NO:62) |
| 5' ATATGATCATTAGACTTCTAC | (SEQ ID NO:63) |
| 5' CTGTTACAGAAGATGTTAAGT | (SEQ ID NO:64) |
| 5' GCAACAGGAGTACTGACTTCT | (SEQ ID NO:65) |
| 5' CACAAGTATGACTCCTTTCTC | (SEQ ID NO:66) |
| 5' AAATCTTTAGAGTAGTGACAT | (SEQ ID NO:67) |
| 5' TTTCCAAACTTAACAGCAACA | (SEQ ID NO:68) |
| 5' GCATCTTGTGATAGTGTTTAA | (SEQ ID NO:69) |
| 5' ATTGGAAACATCGACAGTGTA | (SEQ ID NO:70) |
| 5' TGCATCATGGAAGATGCATTG | (SEQ ID NO:71) |
| 5' AATGCACTGATACCTGTTTTG | (SEQ ID NO:72) |
| 5' TAAATCCAAGACAGCTTCTTT | (SEQ ID NO:73) |
| 5' TTTGAGATAACACTGCAGTGG | (SEQ ID NO:74) |
| 5' CCAGGTCTGCAGTGCACAAGG | (SEQ ID NO:75) |
| 5' TCGTTATTCAAGCACAGCTTG | (SEQ ID NO:76) |
| 5' TTGCAATGTGATATGGACTGC | (SEQ ID NO:77) |
| 5' ATTGGCTTCAAGACTGAGATA | (SEQ ID NO:78) |
| 5' GAGAAGACTGTGTCTCTTAGC | (SEQ ID NO:79) |
| 5' AGAAAGTGAACTCTGATCTTA | (SEQ ID NO:80) |
| 5' GAGCTAAATAGCAGTCCTGAG | (SEQ ID NO:81) |
| 5' TTGGTATATGTACAAGTTTAA | (SEQ ID NO:82) |
| 5' TAGGCTTTGCTGTCTGA | (SEQ ID NO:83) |
| 5' CAGCAAGGATTTGCTGTAT | (SEQ ID NO:84) |
| 5' CCACACTCATACATACACCTC | (SEQ ID NO:85) |
| 5' CATAACTCATAATTGCATTTCG | (SEQ ID NO:86) |
| 5' GTATAATAGGAGAGGTTAGAG | (SEQ ID NO:87) |
| 5' TTCAGCATAAAGCGTTT | (SEQ ID NO:88) |
| 5' AAAGTACTTTAAAATTTCAAA | (SEQ ID NO:89) |
| 5' CCTATGAATTTAGAAATTTCAAA | (SEQ ID NO:90) |
| 5' GGAACATCACTTATAAAATATTTT | (SEQ ID NO:91) |
| 5' ATCTGAGTACCAGGTCTGCA | (SEQ ID NO:92) |

It is also contemplated that any one or more of the foregoing sequences may be combined or excluded with or from any other sequence. Thus, any combination of the foregoing sequences is applicable to the present invention and appended claims.

It is contemplated that oligonucleotides according to the present invention will comprise from about 8 to about 30 nucleic acid base units. It is more preferred that such oligonucleotides will comprise from about 8 and 11 nucleic acid base units, or from about 21 and 30 nucleic acid base units. As will be appreciated, a nucleic acid base unit is a base-sugar combination suitably bound to an adjacent nucleic acid base unit through phosphodiester or the other bonds. It is contemplated that all such oligonucleotides can be synthesized on an automated DNA synthesizer as phosphodiester oligonucleotides or modified oligonucleotides, using standard phosphodiester chemistry, and subsequently purified by HPLC using a reverse phase semiprep C8 column with linear gradient of 5% acetonitrile in 0.1 M trithylammonium acetate and acetonitrile. The purity of the products can be checked by HPLC using an analytical C18 column. Screening of the nucleotide sequences thus produced can be carried out on cell lines expressing cox-1 or cox-2 activities and provided by American Type Culture Collection (ATCC). In such screening, the cells are routinely propagated in culture in a incubator at 37° C. in 5% $CO_2$ and 95% $O_2$ using culture medium according to ATCC recommendations and requirements.

Cells are seeded in 96-well microtiter plates and subsequently treated with various concentrations (0.5 μM, 0.1 or lower) of the antisense and sense oligonucleotides (as controls). After 6, 12, 24, 48 and 72 h of culture, all cells are tested for (a) cytotoxicity using neutral red uptake and MTS assays (55, 56), (b) cyclooxygenase activities (57), prostaglandin synthesis (58) and (c) DNA synthesis stimulation or inhibition by (3H) thymidine uptake assay (59).

Cytotoxicity MTS Assay:

Cells are seeded in 96-well microtiter plates at 2000 cells concentration per well in 200 μl of medium and subsequently treated with various concentrations (0.5 μM, 0.1 or lower) of antisense oligonucleotides. After designated culture time in an incubator at 37° C. with 5% $CO_2$ and 95% $O_2$, 40 μl of MTS solution (mixture of MTS and PMS solutions at ratio 2:0.1) is added to each well and incubated for 2 hours. After this incubation period, the absorbance in each well is measured on the reader at 490 nm to determine the cell metabolic activity (56). The most active oligos are tested for time-dependent cytotoxic effect over a period of five days.

Cytotoxicity NRU Assay:

Cells are seeded in 96-well microtiter plates at 3000 cells concentration per well in 200 μl of medium and subsequently treated with various concentrations (0.5 μM, 0.1 or lower) of antisense oligonucleotides. After designated culture time in a incubator at 37° C. with 5% $CO_2$ and 95% $O_2$, 200 μl of NRU solution (Neutral Red stock solution diluted 1:100 in culture medium) is added to each well and incubated for 2 hours. After this incubation period, the culture medium is discarded and 200 μl of wash/fix solution is added to each well and incubated for 2 minutes. Again solution is discarded on paper towels and 100 μl of diluent solution is added to each well and incubated for 20 minutes in the dark.

The absorbance in each well is measured on the reader at 540 nm to determine the cell metabolic activity (55). The most active oligos are tested for time-dependent cytotoxic effect over a period of five days.

$^3$H-Thymidine Uptake Assay:

Cells are distributed on 96-well plastic plate as described for MTS assay at the same cell density and cultured in the same conditions. Then cells are immediately treated with various concentrations (0.5 μM, 0.1 or lower) of antisense oligonucleotides. After designated culture time in a incubator at 37° C. with 5% $CO_2$ and 95% $O_2$, 1 μCi of $^3$H-Thymidine is added to each well and incubated for an additional 2 h. Cells are then harvested on automatic harvester and $^3$H-Thymidine incorporation is measured in a beta-counter.

Prostaglandin Production and Cox Activity Assays:

The determination of prostaglandin E2, prostaglandin D2 and prostaglandin F2alpha production in culture media is performed after designated incubation time with antisense oligonucleotides. Media are first centrifuged at 2000 rpm for 5 minutes and transfer to new tubes. The levels of prostaglandin production are measured by specific radioimmunoassay using monoclonal antibodies. All samples are evaluated in triplicates and correlated to standard curves.

Cox activity is measured in cell cultures for designated periods of time exposure to antisense oligonucleotides described above. Immediately after oligos treatment, cells are pulsed with 1 μCi of $^3$H-arachidonic acid and incubated at 37° C. with 5% $CO_2$ and 95% $O_2$ and eicosanoids production is analyzed by HPLC TLC chromatographies.

The sequence specificity can be advantageously examined using RT-PCR (60), starting from the isolation of total cellular RNA, than synthesis of cDNA using reverse transcription method and amplification of target DNA using specific primers. The amount of PCR product can be examined by hybridization with specific radiolabelled probe and southern blot analysis (59).

RNA Isolation Method:

Cell cultures are first placed on ice, culture mediums are removed and cells are washed with cold PBS. Then 0.5 ml of lyses buffer is added to cells and the lysate is collected to new tubes using cell scrapers. All samples are diluted with the same volume of 70% ethanol, mix well, transfer on spin column (Qiagen) and spin for 15 sec. at 10,000 rpm. Next, columns are washed with 0.7 ml of RW1 buffer and spin as described above. Then again washed twice with RPE buffer and spin down first 15 sec. and second 2 minutes. RNA is eluted from the column by applying 50 μl of water and spinning down for 1 minute.

Reverse Transcription Reaction:

Total RNA 1 μl (0.5 μg/μl) is mixed with oligo dT primer 1 μl (0.5 μg/μl) and 10 μl of water, heated at 70° C. for 10 minutes and cooled on ice. First strand cDNA is synthesized by adding to the reaction 4 μl of 5x first strand buffer, 2 μl of 0.1M DTT, 1 μl of 10 mM dNTP mix and 1 μl of reverse transcriptase enzyme. Mixture is incubated at 42° C. for 2 hours and cDNAs are used for PCR amplification.

In a preferred systemic application, the oligos may be administered intravenously in a dose of 1 to 100 mg/kg once per day. In a preferred topical application, the oligos may be administered in a 1–5% solution once per day.

REFERENCES

1. Hemler M. et al, (1976) J. Biol. Chem., 251, 5575.
2. DeWitt D. L. et al., (1988) Proc. Natl. Acad. Sci. USA, 85, 1412.
3. Yokoyama C. et al., (1989) Biochem. Biophys. Res. Commun., 165, 888.
4. Herschman H. R., (1996) Biochim. Biophys. Acta, 1299, 125.
5. DeWitt D. L., (1991) Biochim. Biophys. Acta, 1083, 121.
6. Masferrer J. L. et al., (1990), J. Clin. Invest., 86, 1375.
7. Xie W., et al., (1991) Proc. Natl. Acad. Sci. USA 88, 2692.
8. Jones D. A., et al., (1993) J. Biol. Chem. 268, 9049.
9. Tazawa R., et al., (1994) Biochem. Biophys. Res. Commun., 203, 190.
10. Appleby S. B., et al., (1994) Biochem. J. 302, 723.
11. Kujubu D. A., et al., (1991) J. Biol. Chem. 266, 12866.
12. Morita I., et al., (1995) J. Biol. Chem. 270, 10902.
13. Otto J. C., Smith W. L., (1995) J. Lipid Mediat. Cell Signal. 12, 139.
14. O'Neil G. P., Ford-Hutchinson A. W., (1993) FEBS Letters 330, 156.
15. Bakhle Y. S., Botting R. M., (1996) Mediat. Inflamm. 5, 305.
16. Antiplatelet Trialists' Collaboration, (1994) Br. Med. J. 308, 81.
17. Smith W. L. and Marnett L. J., (1991) Biochim. Biophys. Acta 1083, 1.
18. Herschman H. R., (1994) in Cancer and Metastasis Reviews, Vol.13, 241.
19. Kargman S., et al., (1996) Gastroenterology 111, 445.
20. Roth G. J., et al., (1975) Proc. Natl. Acad. Sci. USA 72, 3075.
21. Shimokawa T. and Smith W. L., (1992) J. Biol. Chem. 267, 12387.
22. Peri K. G., et al., (1995) J. Biol. Chem. 270, 24615.
23. Garcia-Rodriguez L. A. and Jick H., (1994) Lancet 343, 769.
24. Sawdy R., et al., (1997) Lancet 350, 265.
25. Chakraborty I., et al., (1996) J. Mol. Endocrinol. 16, 107.
26. Trautman M. S., et al., (1996) Placenta 17, 239.
27. Gibb W., Sun M., (1996) J. Endocrinol. 150, 497.
28. Langenbach R., et al., (1995) Cell, 83, 483.
29. Morham S. G. et al., (1995) Cell 83, 473.
30. Dinchuk J. E. et al., (1995) Nature 378, 406.
31. Breder C. D. et al., (1995) J. Comp. Neurol. 355, 296.
32. Yamagata K. et al., (1993) Neuron 11, 371.
33. Cao C. et al., (1996) Brain Res. 733, 263.
34. Ferreira S. H., (1972) Nature 240, 200.
35. Malmberg A. B., Yaksh T. L., (1992) Science 257, 1276.
36. Vane J. R., Botting R. M., (1994) In Lipid Mediators, ed. F. Cunningham, 61.
37. Sano H. et al., (1992) J. Clin. Invest. 89, 97.
38. Crofford L. J. et al., (1994) J. Clin. Invest. 93, 1095.
39. Jackson L. M. et al., (1998) Gastroenterology 114, A1 60.
40. Harris R. C. et al., (1994) J. Clin. Invest. 94, 2504.
41. Thun M. J. et al., (1991) N. Engl. J. Med. 325, 1593.
42. Schreinemachers D. M., Everson R. B., (1994) Epidemiology 5, 138.
43. Guengerich F. P., (1988) Cancer Res. 48, 2946.
44. Parrett M. L. et al., (1997) Int. J. Oncol. 10, 503.
45. Eberhart C. E. et al., (1994) Gastroenterology 107, 1183.
46. Breitner J. C. S., (1996) Expert. Opin. Invest. Drugs 5, 449.
47. McGeer P. L., McGeer E. G., (1995) Brain Res. Rev. 21, 195.
48. Stewart W. F. et al., (1997) Neurology 48, 626.
49. Dickson D. W. et al., (1993) Glia 7, 75.
50. Eikelenboom P. et al., (1989) Virchows Archiv. B. Cell Pathol. 56, 259.
51. Akiyama H. et al., (1993) Acta Neuropathol. 85, 628.
52. Abraham C. A. et al., (1988) Cell 52, 487.
53. Pasinetti G. M., (1999) IBC's Second Annual Conference on Cox-2 Inhibitors, San Diego, April 12–13.

54. Koistinaho J., (1999) IBC's Second Annual Conference on Cox-2 Inhibitors, San Diego, April 12–13.
55. Borenfreund E. et al., (1985) Toxicol. Lett. 24, 119.
56. Ponsoda R. J. et al., (1994) Toxic. In Vitro 8, 47.
57. Funk C. D. et al., (1991) FASEB J. 5,2304.
58. Masferrer J. L. et al., (1990) J. Clin. Invest. 86, 1375.
59. Angel J. et al., (1994) Eur. J. Biochem. 226, 125.
60. Olbina G. et al., Anticancer Res. (1995),60.
61. Innis M. A. et al., (1990) PCR Protocols, Academic Press, 1–70.
62. McAdam B. F. et al., (1999) Proc. Natl. Acad. Sci. USA 96, 272.
63. Braden G. A. et al., (1991) Circulation 84, 679.
64. FitzGerald G. A. et al., (1984) N. Engl. J. Med. 310, 165.
65. FitzGerald D. J. et al., (1986) N. Engl. J. Med. 315, 983.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

What is claimed is:

1. A method of inhibiting production of COX-2, comprising contacting a sample in vitro comprising a polynucleotide encoding COX-2 with an inhibiting effective amount of COX-2 antisense oligonucleotide, wherein said antisense oligonucleotide selectively hybridizes under physiologic conditions with a polynucleotide encoding a COX-2, thereby inhibiting the COX-2 production, wherein the antisense oligonucleotide has a length of between about 21 to about 30 nucleotides in length and comprises a contiguous nucleic acid sequence selected from the group consisting of SEQ ID NO:1, SEQ ID NO:2, SEQ ID NO:3, SEQ ID NO:4, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO:26, SEQ ID NO:28, SEQ ID NO:29, SEQ ID NO:31, SEQ ID NO:33, SEQ ID NO:34, SEQ ID NO:35, SEQ ID NO:36, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:85, SEQ ID NO:86, SEQ ID NO:87, SEQ ID NO:89, SEQ ID NO:90 and SEQ ID NO:91.

2. The method of claim 1, wherein the antisense oligonucleotide is in an expression vector.

3. The method of claim 2, wherein the vector is a plasmid.

4. The method of claim 2, wherein the vector is a viral vector.

5. The method of claim 1, wherein the antisense oligonucleotide is chemically modified.

6. The method of claim 5, wherein the chemical modification is conjugation of the antisense oligonucleotide at the 3' or the 5' end to another molecule selected from the group consisting of a sugar, a peptide and a polymer.

7. The method of claim 5, wherein the chemical modification is by substitution in a non-bridging oxygen atom of the antisense oligonucleotide back bone with a moiety selected from the group consisting of a methane phosphate, a methyl phosphate, a phosphoramidite and a phosphorothioate.

8. The method of claim 5, wherein at least a portion of a ribose sugar residue or a deoxyribose sugar residue is chemically modified at a 2', a 3' or a 5' position.

9. The method of claim 5, 7, or 8, wherein the modification is at the 5' terminal region, the 3' terminal region, between the 5' and 3' terminal region or a combination thereof.

10. The method of claim 1, wherein the antisense oligonucleotide is DNA.

11. The method of claim 1, wherein the antisense oligonucleotide is RNA.

12. The method of claim 1, wherein the sample contains cells or cells in culture.

13. The method of claim 1, wherein the sample is a tissue.

14. An antisense oligonucleotide of about 21 to about 30 nucleotides in length comprising a contiguous nucleic acid sequence selected from the group consisting of SEQ ID NO:1, SEQ ID NO:2, SEQ ID NO:3, SEQ ID NO:4, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO:26, SEQ ID NO:28, SEQ ID NO:29, SEQ ID NO:31, SEQ ID NO:33, SEQ ID NO:34, SEQ ID NO:35, SEQ ID NO:36, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:85, SEQ ID NO:86, SEQ ID NO:87, SEQ ID NO:89, SEQ ID NO:90 and SEQ ID NO:91,
wherein the antisense oligonucleotide selectively hybridizes to a COX-2 polynucleotide under physiologic conditions.

15. The antisense oligonucleotide of claim 14, wherein the oligonucleotide is chemically modified.

16. The antisense oligonucleotide of claim 15, wherein the chemical modification is conjugation of the antisense oligonucleotide at the 3' or the 5' end to another molecule selected from the group consisting of a sugar, a peptide and a polymer.

17. The antisense oligonucleotide of claim 15, wherein the chemical modification is by substitution in a non-bridging oxygen atom of the antisense oligonucleotide backbone with a moiety selected from the group consisting of a methane phosphate, a methyl phosphate, a phosphoramidite and a phosphorothioate.

18. The antisense oligonucleotide of claim 15, wherein at least a portion of a ribose sugar residue or a deoxyribose sugar residue is chemically modified at a 2', a 3' or a 5' position.

19. The antisense oligonucleotide of claim 15, 17, or 18, wherein the modification is at the 5' terminal region, the 3' terminal region, between the 5' and 3' terminal region or a combination thereof.

20. The antisense oligonucleotide of claim 14, wherein the antisense oligonucleotide is DNA.

21. The antisense oligonucleotide of claim 14, wherein the antisense oligonucleotide is RNA.

22. The antisense oligonucleotide of claim 14, wherein the antisense oligonucleotide is contained in a vector.

23. The antisense oligonucleotide of claim 22, wherein the vector is an expression vector.

24. The antisense oligonucleotide of claim 22, wherein the vector is a plasmid.

25. The antisense oligonucleotide of claim 22, wherein the vector is a viral vector.

26. A composition comprising an antisense oligonucleotide having a length of between about 21 to about 30 nucleotides and comprising a contiguous nucleic acid sequence selected from the group consisting of SEQ ID NO:1, SEQ ID NO:2, SEQ ID NO:3, SEQ ID NO:4, SEQ ID NO:7, SEQ ID NO:8, SEQ ID NO:9, SEQ ID NO:10, SEQ ID NO:11, SEQ ID NO:12, SEQ ID NO:13, SEQ ID NO:15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, SEQ ID NO: 24, SEQ ID NO: 25, SEQ ID NO:26, SEQ ID NO:28, SEQ ID NO:29, SEQ ID NO:31, SEQ ID NO:33, SEQ ID NO:34, SEQ ID NO:35, SEQ ID NO:36, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:85, SEQ ID NO:86, SEQ ID NO:87, SEQ ID NO:89, SEQ ID NO:90 and SEQ ID NO:91, and a pharmaceutically accepted carrier.

27. An antisense oligonucleotide no longer than about 30 nucleotides in length comprising a contiguous nucleic acid sequence selected from the group consisting of SEQ ID NO:1, SEQ ID NO:2, SEQ ID NO:3, SEQ ID NO:4, SEQ ID NO:7, SEQ ID NO:8, SEQ ID NO:9, SEQ ID NO:10, SEQ ID NO:11, SEQ ID NO:12, wherein the antisense oligonucleotide selectively hybridizes to a COX-2 polynucleotide under physiologic conditions.

28. An antisense oligonucleotide no longer than about 30 nucleotides in length comprising a contiguous nucleic acid sequence selected from the group consisting of SEQ ID NO:13, SEQ ID NO:15, SEQ ID NO: 16, SEQ ID NO:17, SEQ ID NO: 18, SEQ ID NO: 19, SEQ ID NO:20, SEQ ID NO: 21, SEQ ID NO: 22, SEQ ID NO: 23, wherein the antisense oligonucleotide selectively hybridizes to a COX-2 polynucleotide under physiologic conditions.

29. An antisense oligonucleotide no longer than about 30 nucleotides in length comprising a contiguous nucleic acid sequence selected from the group consisting of SEQ ID NO: 24, SEQ ID NO: 25, SEQ ID NO:26, SEQ ID NO:28, SEQ ID NO:29, SEQ ID NO:31, SEQ ID NO:33, SEQ ID NO:34, SEQ ID NO:35, SEQ ID NO:36, SEQ ID NO:37, SEQ ID NO:39, wherein the antisense oligonucleotide selectively hybridizes to a COX-2 polynucleotide under physiologic conditions.

30. An antisense oligonucleotide no longer than about 30 nucleotides in length comprising a contiguous nucleic acid sequence selected from the group consisting of SEQ ID NO:40, SEQ ID NO:41, SEQ ID NO:42, SEQ ID NO:43, SEQ ID NO:44, SEQ ID NO:45, SEQ ID NO:46, SEQ ID NO:48, SEQ ID NO:49, SEQ ID NO:50, wherein the antisense oligonucleotide selectively hybridizes to a COX-2 polynucleotide under physiologic conditions.

31. An antisense oligonucleotide no longer than about 30 nucleotides in length comprising a contiguous nucleic acid sequence selected from the group consisting of SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:60, SEQ ID NO:61, wherein the antisense oligonucleotide selectively hybridizes to a COX-2 polynucleotide under physiologic conditions.

32. An antisense oligonucleotide no longer than about 30 nucleotides in length comprising a contiguous nucleic acid sequence selected from the group consisting of SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, wherein the antisense oligonucleotide selectively hybridizes to a COX-2 polynucleotide under physiologic conditions.

33. An antisense oligonucleotide no longer than about 30 nucleotides in length comprising a contiguous nucleic acid sequence selected from the group consisting of SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, wherein the antisense oligonucleotide selectively hybridizes to a COX-2 polynucleotide under physiologic conditions.

34. An antisense oligonucleotide no longer than about 30 nucleotides in length comprising a contiguous nucleic acid sequence selected from the group consisting of SEQ ID NO:82, SEQ ID NO:85, SEQ ID NO:86, SEQ ID NO:87, SEQ ID NO:89, SEQ ID NO:90 and SEQ ID NO:91, wherein the antisense oligonucleotide selectively hybridizes to a COX-2 polynucleotide under physiologic conditions.

35. An antisense oligonucleotide no longer than about 30 nucleotides in length comprising a contiguous nucleic acid sequence selected from the group consisting of SEQ ID NO:4, SEQ ID NO:5, SEQ ID NO:14, SEQ ID NO:27, SEQ ID NO:30, SEQ ID NO:32, SEQ ID NO:38, SEQ ID NO:47, SEQ ID NO:59, SEQ ID NO:83, SEQ ID NO:84, SEQ ID NO:88 and SEQ ID NO:92, wherein the antisense oligonucleotide selectively hybridizes to a COX-2 polynucleotide under physiologic conditions.

* * * * *

SEQUENCE LISTING

<160> NUMBER OF SEQ ID NOS: 92

<210> SEQ ID NO 1
<211> LENGTH: 21
<212> TYPE: DNA
<213> ORGANISM: Artificial Sequence
<220> FEATURE:
<223> OTHER INFORMATION: Synthetically generated antisense oligonucleotides

<400> SEQUENCE: 1
aaggatttgc tgtatggctg a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetically generated antisense oligonucleotides

<400> SEQUENCE: 2
acagcaagga tttgctgtat g                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetically generated antisense oligonucleotides

<400> SEQUENCE: 3
cacactcata catacacctc g                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetically generated antisense oligonucleotides

<400> SEQUENCE: 4
gcacttatac tggtcaaatc c                                              21

<210> SEQ ID NO 5
<211> LENGTH: 20
<212> TYPE: DNA

```
<213> ORGANISM: Artificial Sequence
<220> FEATURE:
<223> OTHER INFORMATION: Synthetically generated antisense
      oligonucleotides

<400> SEQUENCE: 5
ggtacaatcg cacttatctg                                              20

<210> SEQ ID NO 6
<211> LENGTH: 14
<212> TYPE: DNA
<213> ORGANISM: Artificial Sequence
<220> FEATURE:
<223> OTHER INFORMATION: Synthetically generated antisense
      oligonucleotides

<400> SEQUENCE: 6
ctttgctgtc tgag                                                    14

<210> SEQ ID NO 7
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 7
ggtaggcttt gctgtctgag g                                            21

<210> SEQ ID NO 8
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 8
gctgctgagg agttcctgga c                                            21

<210> SEQ ID NO 9
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 9
ctggctgtgg agctgaagga g                                            21

<210> SEQ ID NO 10
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 10
cagttttctc catagaatcc t                                            21

<210> SEQ ID NO 11
<211> LENGTH: 22
<212> TYPE: DNA
<213> ORGANISM: Artificial Sequence
```

```
<220> FEATURE:
<223> OTHER INFORMATION: Synthetically generated antisense
      oligonucleotides

<400> SEQUENCE: 11
ttttattctt gtcaaaaatt cc                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetically generated antisense
      oligonucleotides

<400> SEQUENCE: 12
ggtttcagaa ataattttat tc                                              22

<210> SEQ ID NO 13
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 13
tatgtagtgc actgtgtttg g                                               21

<210> SEQ ID NO 14
<211> LENGTH: 13
<212> TYPE: DNA
<213> ORGANISM: Artificial Sequence
<220> FEATURE:
<223> OTHER INFORMATION: Synthetically generated antisense
      oligonucleotides

<400> SEQUENCE: 14
cccttgaagt ggg                                                        13

<210> SEQ ID NO 15
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 15
gaatgttatt cacaacgttc c                                               21

<210> SEQ ID NO 16
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 16
ctcataattg catttcgaag g                                               21

<210> SEQ ID NO 17
<211> LENGTH: 22
<212> TYPE: DNA
<213> ORGANISM: Artificial Sequence
<220> FEATURE:
```

<223> OTHER INFORMATION: Synthetically generated antisense
      oligonucleotides

<400> SEQUENCE: 17
atgtgatctg gatgtcaaca ca                                              22

<210> SEQ ID NO 18
<211> LENGTH: 22
<212> TYPE: DNA
<213> ORGANISM: Artificial Sequence
<220> FEATURE:
<223> OTHER INFORMATION: Synthetically generated antisense
      oligonucleotides

<400> SEQUENCE: 18
tagtcagcat tgtaagttgg tg                                              22

<210> SEQ ID NO 19
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 19
aataggagag gttagagaag g                                               21

<210> SEQ ID NO 20
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 20
cacaatctca tttgaatcag g                                               21

<210> SEQ ID NO 21
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 21
gatgaacttt cttcttagaa g                                               21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 22
tcgcttatga tctgtcttga a                                               21

<210> SEQ ID NO 23
<211> LENGTH: 21
<212> TYPE: DNA

```
<213> ORGANISM: Artificial Sequence
<220> FEATURE:
<223> OTHER INFORMATION: Synthetically generated antisense
      oligonucleotides

<400> SEQUENCE: 23
gtaaatatga tttaagtcca c                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 24
ctgtctagcc agagtttcac c                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 25
tcatttttcc atccttgaaa a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 26
ccatcaatta tctgatattt g                                              21

<210> SEQ ID NO 27
<211> LENGTH: 20
<212> TYPE: DNA
<213> ORGANISM: Artificial Sequence
<220> FEATURE:
<223> OTHER INFORMATION: Synthetically generated antisense
      oligonucleotides

<400> SEQUENCE: 27
gaggatacat ctctccatca                                                20

<210> SEQ ID NO 28
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 28
cctgagtatc tttgactgtg g                                              21

<210> SEQ ID NO 29
<211> LENGTH: 21
<212> TYPE: DNA
<213> ORGANISM: Artificial Sequence
```

```
<220> FEATURE:
<223> OTHER INFORMATION: Synthetically generated antisense
      oligonucleotides

<400> SEQUENCE: 29
aggagggtag atcatctctg c                                              21

<210> SEQ ID NO 30
<211> LENGTH: 20
<212> TYPE: DNA
<213> ORGANISM: Artificial Sequence
<220> FEATURE:
<223> OTHER INFORMATION: Synthetically generated antisense
      oligonucleotides

<400> SEQUENCE: 30
gcaaaccgta gatgctcagg                                                20

<210> SEQ ID NO 31
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 31
caccagacca aagacctcct g                                              21

<210> SEQ ID NO 32
<211> LENGTH: 13
<212> TYPE: DNA
<213> ORGANISM: Artificial Sequence
<220> FEATURE:
<223> OTHER INFORMATION: Synthetically generated antisense
      oligonucleotides

<400> SEQUENCE: 32
cagaccaggc acc                                                       13

<210> SEQ ID NO 33
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 33
atcatcagac caggcaccag a                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 34
ctcagccaga ttgtggcata c                                              21

<210> SEQ ID NO 35
<211> LENGTH: 21
<212> TYPE: DNA
<213> ORGANISM: Artificial Sequence
<220> FEATURE:
```

<223> OTHER INFORMATION: Synthetically generated antisense
     oligonucleotides

<400> SEQUENCE: 35
tcgcattact ctgttgtgtt c                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetically generated antisense
     oligonucleotides

<400> SEQUENCE: 36
atgctcctgt ttaagcacat c                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetically generated antisense
     oligonucleotides

<400> SEQUENCE: 37
cttgtctgga acaactgctc a                                              21

<210> SEQ ID NO 38
<211> LENGTH: 19
<212> TYPE: DNA
<213> ORGANISM: Artificial Sequence
<220> FEATURE:
<223> OTHER INFORMATION: Synthetically generated antisense
     oligonucleotides

<400> SEQUENCE: 38
agtctcctat cagtattag                                                 19

<210> SEQ ID NO 39
<211> LENGTH: 21
<212> TYPE: DNA
<213> ORGANISM: Artificial Sequence
<220> FEATURE:
<223> OTHER INFORMATION: Synthetically generated antisense
     oligonucleotides

<400> SEQUENCE: 39
tgttgcacat aatcttcaat c                                              21

<210> SEQ ID NO 40
<211> LENGTH: 21
<212> TYPE: DNA
<213> ORGANISM: Artificial Sequence
<220> FEATURE:
<223> OTHER INFORMATION: Synthetically generated antisense
     oligonucleotides

<400> SEQUENCE: 40
gtttgttgaa aagtagttct g                                              21

<210> SEQ ID NO 41
<211> LENGTH: 21
<212> TYPE: DNA

```
<213> ORGANISM: Artificial Sequence
<220> FEATURE:
<223> OTHER INFORMATION: Synthetically generated antisense
      oligonucleotides

<400> SEQUENCE: 41
aattgtttgt tgaaaagtag t                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 42
ggtgttaaat tcagcagcaa t                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 43
tttctggtca tgaatttgaa a                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 44
atagagttgt tgtagataaa c                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 45
ctgttgatag ttgtatttct g                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 46
ggtgaatgat tcaacaaact g                                              21

<210> SEQ ID NO 47
<211> LENGTH: 16
<212> TYPE: DNA
<213> ORGANISM: Artificial Sequence
```

```
<220> FEATURE:
<223> OTHER INFORMATION: Synthetically generated antisense
      oligonucleotides

<400> SEQUENCE: 47
gatactttct gtactg                                                       16

<210> SEQ ID NO 48
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 48
cctgtgatac tttctgtact g                                                 21

<210> SEQ ID NO 49
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 49
cctgctctgg tcaatggaag c                                                 21

<210> SEQ ID NO 50
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 50
aaaagactgg tatttcatct g                                                 21

<210> SEQ ID NO 51
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 51
gttcttcaaa tgattcatag g                                                 21

<210> SEQ ID NO 52
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 52
tcgatgtcac catagagtgc t                                                 21

<210> SEQ ID NO 53
<211> LENGTH: 21
<212> TYPE: DNA
<213> ORGANISM: Artificial Sequence
<220> FEATURE:
```

```
<223> OTHER INFORMATION: Synthetically generated antisense
      oligonucleotides

<400> SEQUENCE: 53
cttctaccat ggtttcacca a                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 54
tgctccaact tctaccatgg t                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 55
gtcctttcaa ggagaatggt g                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 56
cagtgttgat gatttgaaaa c                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 57
tgcagatgag agactgaatt g                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 58
gaacactgaa tgaagtaaag g                                              21

<210> SEQ ID NO 59
<211> LENGTH: 20
<212> TYPE: DNA
```

```
<213> ORGANISM: Artificial Sequence
<220> FEATURE:
<223> OTHER INFORMATION: Synthetically generated antisense
      oligonucleotides

<400> SEQUENCE: 59
tttaatgagc tctggatctg                                               20

<210> SEQ ID NO 60
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 60
aacttgcatt gatggtgact g                                             21

<210> SEQ ID NO 61
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 61
tgggattgat atcatctagt c                                             21

<210> SEQ ID NO 62
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 62
tacagttcag tcgaacgttc t                                             21

<210> SEQ ID NO 63
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 63
atatgatcat tagacttcta c                                             21

<210> SEQ ID NO 64
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 64
ctgttacaga agatgttaag t                                             21

<210> SEQ ID NO 65
<211> LENGTH: 21
<212> TYPE: DNA
<213> ORGANISM: Artificial Sequence
```

```
<220> FEATURE:
<223> OTHER INFORMATION: Synthetically generated antisense
      oligonucleotides

<400> SEQUENCE: 65
gcaacaggag tactgacttc t                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 66
cacaagtatg actcctttct c                                              21

<210> SEQ ID NO 67
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 67
aaatctttag agtagtgaca t                                              21

<210> SEQ ID NO 68
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 68
tttccaaact taacagcaac a                                              21

<210> SEQ ID NO 69
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 69
gcatcttgtg atagtgttta a                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 70
attggaaaca tcgacagtgt a                                              21

<210> SEQ ID NO 71
<211> LENGTH: 21
<212> TYPE: DNA
<213> ORGANISM: Artificial Sequence
<220> FEATURE:
```

```
<223> OTHER INFORMATION: Synthetically generated antisense
      oligonucleotides

<400> SEQUENCE: 71
tgcatcatgg aagatgcatt g                                              21

<210> SEQ ID NO 72
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 72
aatgcactga tacctgtttt g                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 73
taaatccaag acagcttctt t                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 74
tttgagataa cactgcagtg g                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 75
ccaggtctgc agtgcacaag g                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 76
tcgttattca agcacagctt g                                              21

<210> SEQ ID NO 77
<211> LENGTH: 21
<212> TYPE: DNA
```

```
<213> ORGANISM: Artificial Sequence
<220> FEATURE:
<223> OTHER INFORMATION: Synthetically generated antisense
      oligonucleotides

<400> SEQUENCE: 77
ttgcaatgtg atatggactg c                                             21

<210> SEQ ID NO 78
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 78
attggcttca agactgagat a                                             21

<210> SEQ ID NO 79
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 79
gagaagactg tgtctcttag c                                             21

<210> SEQ ID NO 80
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 80
agaaagtgaa ctctgatctt a                                             21

<210> SEQ ID NO 81
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 81
gagctaaata gcagtcctga g                                             21

<210> SEQ ID NO 82
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 82
ttggtatatg tacaagttta a                                             21

<210> SEQ ID NO 83
<211> LENGTH: 17
<212> TYPE: DNA
<213> ORGANISM: Artificial Sequence
```

```
<220> FEATURE:
<223> OTHER INFORMATION: Synthetically generated antisense
      oligonucleotides

<400> SEQUENCE: 83
taggctttgc tgtctga                                                17

<210> SEQ ID NO 84
<211> LENGTH: 19
<212> TYPE: DNA
<213> ORGANISM: Artificial Sequence
<220> FEATURE:
<223> OTHER INFORMATION: Synthetically generated antisense
      oligonucleotides

<400> SEQUENCE: 84
cagcaaggat ttgctgtat                                              19

<210> SEQ ID NO 85
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 85
ccacactcat acatacacct c                                           21

<210> SEQ ID NO 86
<211> LENGTH: 22
<212> TYPE: DNA
<213> ORGANISM: Artificial Sequence
<220> FEATURE:
<223> OTHER INFORMATION: Synthetically generated antisense
      oligonucleotides

<400> SEQUENCE: 86
cataactcat aattgcattt cg                                          22

<210> SEQ ID NO 87
<211> LENGTH: 21
<212> TYPE: DNA
<213> ORGANISM: Artificial Sequence
<220> FEATURE:
<223> OTHER INFORMATION: Synthetically generated antisense
      oligonucleotides

<400> SEQUENCE: 87
gtataatagg agaggttaga g                                           21

<210> SEQ ID NO 88
<211> LENGTH: 17
<212> TYPE: DNA
<213> ORGANISM: Artificial Sequence
<220> FEATURE:
<223> OTHER INFORMATION: Synthetically generated antisense
      oligonucleotides

<400> SEQUENCE: 88
ttcagcataa agcgttt                                                17

<210> SEQ ID NO 89
<211> LENGTH: 21
<212> TYPE: DNA
<213> ORGANISM: Artificial Sequence
<220> FEATURE:
```

<223> OTHER INFORMATION: Synthetically generated antisense
      oligonucleotides

<400> SEQUENCE: 89
aaagtacttt aaaatttcaa a                                              21

<210> SEQ ID NO 90
<211> LENGTH: 23
<212> TYPE: DNA
<213> ORGANISM: Artificial Sequence
<220> FEATURE:
<223> OTHER INFORMATION: Synthetically generated antisense
      oligonucleotides

<400> SEQUENCE: 90
cctatgaatt tagaaatttc aaa                                            23

<210> SEQ ID NO 91
<211> LENGTH: 24
<212> TYPE: DNA
<213> ORGANISM: Artificial Sequence
<220> FEATURE:
<223> OTHER INFORMATION: Synthetically generated antisense
      oligonucleotides

<400> SEQUENCE: 91
ggaacatcac ttataaaata tttt                                           24

<210> SEQ ID NO 92
<211> LENGTH: 20
<212> TYPE: DNA
<213> ORGANISM: Artificial Sequence
<220> FEATURE:
<223> OTHER INFORMATION: Synthetically generated antisense
      oligonucleotides

<400> SEQUENCE: 92
atctgagtac caggtctgca                                                20